United States Patent
Mizrahi et al.

(10) Patent No.: US 11,529,051 B2
(45) Date of Patent: *Dec. 20, 2022

(54) CONTROLLING ELECTROMAGNETIC (EM) TRANSMISSION BASED ON PRESSURE PARAMETERS

(71) Applicant: Sensible Medical Innovations Ltd., Netanya (IL)

(72) Inventors: Nadav Mizrahi, Tel-Aviv (IL); Dan Rappaport, Tel-Aviv (IL); Amir Saroka, Herzlia (IL); Oren Kalisman, Tel-Aviv (IL); Yiftach Barash, Tel-Aviv (IL); Tal Levi, Tel-Aviv (IL); Yaron Adler, Shoham (IL)

(73) Assignee: Sensible Medical Innovations Ltd., Netanya (IL)

( * ) Notice: Subject to any disclaimer, the term of this patent is extended or adjusted under 35 U.S.C. 154(b) by 196 days.

This patent is subject to a terminal disclaimer.

(21) Appl. No.: 16/840,639

(22) Filed: Apr. 6, 2020

(65) Prior Publication Data

US 2020/0229696 A1 Jul. 23, 2020

Related U.S. Application Data

(63) Continuation of application No. 14/901,161, filed as application No. PCT/IL2013/050544 on Jun. 26, 2013, now Pat. No. 10,610,100.

(51) Int. Cl.
*A61B 5/00* (2006.01)
*A61B 5/0507* (2021.01)
(Continued)

(52) U.S. Cl.
CPC .............. *A61B 5/0017* (2013.01); *A61B 5/02* (2013.01); *A61B 5/0507* (2013.01); *A61B 5/08* (2013.01);
(Continued)

(58) Field of Classification Search
CPC combination set(s) only.
See application file for complete search history.

(56) References Cited

U.S. PATENT DOCUMENTS

| 10,610,100 B2* | 4/2020 | Mizrahi | A61B 5/0507 |
| 2003/0212335 A1* | 11/2003 | Huang | A61B 6/4233 |
| | | | 600/500 |

(Continued)

FOREIGN PATENT DOCUMENTS

| CN | 1011296260 | 2/2008 |
| CN | 103068302 | 4/2013 |
| EP | 0377554 | 7/1990 |

OTHER PUBLICATIONS

Office Action dated Jul. 29, 2020 From the Israel Patent Office Re. Application No. 243342. (4 Pages).
(Continued)

*Primary Examiner* — Joel F Brutus (57) ABSTRACT

A method of controlling an analysis of electromagnetic (EM) signal of a human subject. The method comprises positioning an EM transducer unit in front of a skin area above a target intrabody volume of a human subject, the EM transducer unit having at least one EM transducer, a pressure applying unit that applies a variable pressure on the skin area, and a pressure sensor, measuring at least one pressure parameter indicative of the variable pressure using the pressure sensor, capturing EM signal using the at least one EM transducer, and performing an analysis of the EM signal to infer at least one intrabody parameter of the target intrabody volume. The analysis is controlled according to the at least one pressure parameter.

20 Claims, 8 Drawing Sheets

(51) Int. Cl.
  *A61B 5/02* (2006.01)
  *A61B 5/08* (2006.01)
  *A61B 5/0537* (2021.01)
  *A61B 5/113* (2006.01)

(52) U.S. Cl.
  CPC ............ *A61B 5/684* (2013.01); *A61B 5/6843* (2013.01); *A61B 5/721* (2013.01); *A61B 5/0537* (2013.01); *A61B 5/1135* (2013.01); *A61B 2562/0247* (2013.01)

(56) References Cited

U.S. PATENT DOCUMENTS

| | | | |
|---|---|---|---|
| 2005/0187488 A1 | 8/2005 | Wolf | |
| 2007/0139167 A1* | 6/2007 | Gilson | G09B 21/003 340/407.1 |
| 2008/0033295 A1 | 2/2008 | Matsamura | |
| 2011/0160549 A1* | 6/2011 | Saroka | A61B 5/00 343/700 R |
| 2016/0150959 A1 | 6/2016 | Mizrahi et al. | |

OTHER PUBLICATIONS

Official Action dated Jun. 13, 2019 From the U.S. Appl. No. 14/901,161. (13 Pages).
Official Action dated Sep. 28, 2018 From the U.S. Appl. No. 14/901,161. (47 pages).
Summons to Attend Oral Proceedings Pursuant to Rule 115(1) EPC dated Dec. 11, 2019 From the European Patent Office Re. Application No. 13887640.4. (6 Pages).
Translation dated Mar. 24, 2021 of Office Action dated Jul. 29, 2020 From the Israel Patent Office Re. Application No. 243342. (3 Pages).
Notification of Office Action and Search Report dated Sep. 28, 2022 From the State Intellectual Property Office of the People's Republic of China Re. Application No. 201910571844.4. (5 Pages).
Translation dated Oct. 14, 2022 of Notification of Office Action dated Sep. 28, 2022 From the State Intellectual Property Office of the People's Republic of China Re. Application No. 201910571844.4. (2 Pages).

* cited by examiner

CONTROLLING ELECTROMAGNETIC (EM) TRANSMISSION BASED ON PRESSURE PARAMETERS

RELATED APPLICATIONS

This application is a continuation of U.S. patent application Ser. No. 14/901,161 filed on Dec. 28, 2015, which is a National Phase of PCT Patent Application No. PCT/IL2013/050544 having International Filing Date of Jun. 26, 2013. The content of the above application is all incorporated by reference as if fully set forth herein in their entirety.

FIELD AND BACKGROUND OF THE INVENTION

The present invention, in some embodiments thereof, relates to electromagnetic (EM) transducers and, more particularly, but not exclusively, to controlling EM transmission and/or analysis of EM measurements.

SUMMARY OF THE INVENTION

According to some embodiments of the present invention, there is provided a method of analyzing electromagnetic (EM) signal of a human subject, comprising:

positioning an EM transducer unit in front of a skin area opposite a target intrabody volume of a human subject, the EM transducer unit having at least one EM transducer and at least one pressure sensor;

measuring at least one pressure parameter indicative of a pressure applied on the skin area using the at least one pressure sensor;

measuring EM signal using the at least one EM transducer; and performing an analysis of the EM signal to infer at least one intrabody parameter of the target intrabody volume;

wherein at least one of the analysis, a transmission of the EM signal, and a reception of the EM signal is controlled according to the at least one pressure parameter.

Optionally, the pressure is a variable pressure applied by a pressure applying unit of the EM transducer unit.

Optionally, the target intrabody volume is a thoracic intrabody volume of lungs of the human subject.

Optionally, the method comprises deriving, based on the analysis, a thoracic fluid volume value.

Optionally, the method comprises detecting when the EM transducer unit is properly positioned in front of the skin area by a pressure parameter analysis of the at least one pressure parameter, and transmitting the EM signal when the EM transducer unit is properly positioned in front of the skin area.

Optionally, the method comprises detecting when the EM transducer unit is not properly positioned in front of the skin area by a pressure parameter analysis of the at least one pressure parameter and outputting a notification indicative that the EM transducer unit is not properly positioned in front of the skin area.

Optionally, the method comprises detecting a period during which that the EM transducer unit is improperly positioned in front of the skin area based on a pressure parameter analysis of the at least one pressure parameter and preventing a transmission by the EM transducer unit during the period.

Optionally, the at least one pressure parameter comprises a pressure change pattern.

More optionally, a pressure change pattern is indicative of a breathing process.

More optionally, controlling is used to reduce breathing induced artifacts in EM measurements.

More optionally, the pressure change pattern is indicative of a cardiac system related process.

More optionally, the controlling is used to reduce cardiac system induced artifacts in EM measurements.

More optionally, the controlling is used to separate lung related EM variations from cardiac EM variations.

More optionally, the pressure applying unit comprises an inflatable mechanism; wherein the at least one pressure parameter is measured in an inflatable member of the inflatable mechanism.

More optionally, the pressure applying unit comprises a mechanical element; wherein the at least one pressure parameter is set according to a state of the mechanical element.

Optionally, the at least one pressure parameter comprises a tension of a strip supporting the EM transducer unit at a given location.

Optionally, the EM signal includes radiofrequency (RF) or microwave (MW) radiation.

More optionally, the at least one pressure parameter is of a pressure applied to press the at least one EM transducer on the skin area.

More optionally, the method further comprises controlling the pressure applying unit to maintain the pressure within a predefined range on the skin area.

More optionally, the at least one pressure parameter indicative of a movement of an organ of the human subject; further comprising controlling the pressure applying unit to increase and decrease the pressure synchronically with the movement.

According to some embodiments of the present invention, there is provided a method of performing an analysis of electromagnetic (EM) signal of a human subject, comprising: positioning an EM transducer unit having at least one EM transducer opposite a target intrabody volume of a human subject, and a pressure applying unit that applies pressure on a skin area, capturing EM signal using the at least one EM transducer, calculating instructions for controlling the pressure applying unit based on an analysis of the EM signal, and controlling the pressure applying unit according to the instructions.

More optionally, the method further comprises measuring at least one pressure parameter indicative of the pressure using at least one pressure sensor; wherein the controlling is based on a match between the at least one pressure parameter and the analysis.

More optionally, the instructions comprise instructions to adjust pressure applied by the pressure applying unit on the skin area.

According to some embodiments of the present invention, there is provided an EM transducer unit that comprises an attachment unit for attaching the EM transducer unit in front of a skin opposite to a target intrabody volume of a human subject, at least one EM transducer which transmits and captures EM signal, at least one pressure sensor which measures at least one pressure parameter indicative of a pressure on the skin area using the at least one pressure sensor, and a controller which performs an analysis of the EM signal to infer at least one intrabody parameter of the target intrabody volume. At least one of the analysis, a transmission of the EM signal and a reception of the EM signal is controlled according to the at least one pressure parameter.

Optionally, the pressure is a variable pressure; further comprising a pressure applying unit that applies the variable pressure on the skin area.

According to some embodiments of the present invention, there is provided a method of controlling the transmission of electromagnetic (EM) signal to a human subject. The method comprises positioning an EM transducer unit in front of a skin area opposite a target intrabody volume of a human subject, the EM transducer unit having at least one EM transducer, and at least one pressure sensor, measuring at least one pressure parameter indicative of a pressure applied on the skin area using the at least one pressure sensor, and controlling a transmission of EM signal to the human subject based the at least one pressure parameter.

Optionally, the at least one EM transducer is used for transmitting and receiving the EM signal.

Optionally, the controlling comprises performing the transmission as long as the at least one pressure parameter does not deviate from a pressure threshold.

Optionally, the controlling comprises stopping the transmission when the at least one pressure parameter deviates from a pressure threshold.

According to some embodiments of the present invention, there is provided a method of analyzing electromagnetic (EM) signal of a human subject. The method comprises positioning an EM transducer unit in front of a skin area opposite a target intrabody volume of a human subject, measuring at least one pressure parameter indicative of a pressure applied by an inflatable member of a pneumatic mechanism, and controlling the transmission of EM signal to or from the EM transducer unit based on an analysis of the at least one pressure parameter.

Optionally, the method further comprises performing an analysis of the EM signal to infer at least one intrabody parameter of the target intrabody volume.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

The present invention, in some embodiments thereof, relates to electromagnetic (EM) transducers positioning and, more particularly, but not exclusively, to a thoracic garment of positioning electromagnetic (EM) transducers and methods of using such a thoracic garment.

According to some embodiments of the present invention, there are provided methods and systems of controlling the reception, transmission, and/or analysis of EM signal based on one or more pressure parameters which are indicative of a pressure applied on a skin area of a human subject, for example by a pressure applying unit that applies a variable pressure on the skin area to press one or more EM transducers to the skin area.

Optionally, movement estimation, such as breathing movement estimation, is calculated based on the one or more pressure parameters. In such embodiments, the analysis of the EM signal and/or the transmission and/or reception of the EM signal is performed according to the movement pattern so as to reduce or eliminate artifacts caused by the movement.

According to some embodiments of the present invention, there are provided methods and systems of controlling a pressure applied on a skin area of a subject human based on an analysis of EM signal from an intrabody volume of the human subject. For example, the pressure may be increased and/or decreased to meet the requirements of different states, such as a positioning state, a transmission state, an unwanted disengagement and/or the like.

Optionally, the above outlined pressure is applied using an active or passive mechanism for example, inflatable mechanism, a mechanical mechanism, for example a linear actuator and or a mechanical arm based mechanism, and/or the like. Other examples may include a spring based mechanism, an elastic part of the garment, or a pressure created by the tightening of the garment around the subject's body. Optionally, pressure is applied by or includes taking advantage of object weight, namely placing the EM transducer under the subject's body or vice versa, for example when lying on a bed, or when leaning against a chair backrest.

In use, the pressure may be measured using a sensor. Optionally, the pressure gauge is any sensor that senses parameters that allow calculating the applied forces directly and/or indirectly, for example by measuring a tension on a supporting strip or a vest or measuring pressure at a location different that the location of one or more given EM transducers, with respect of which the sensed data is applied.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
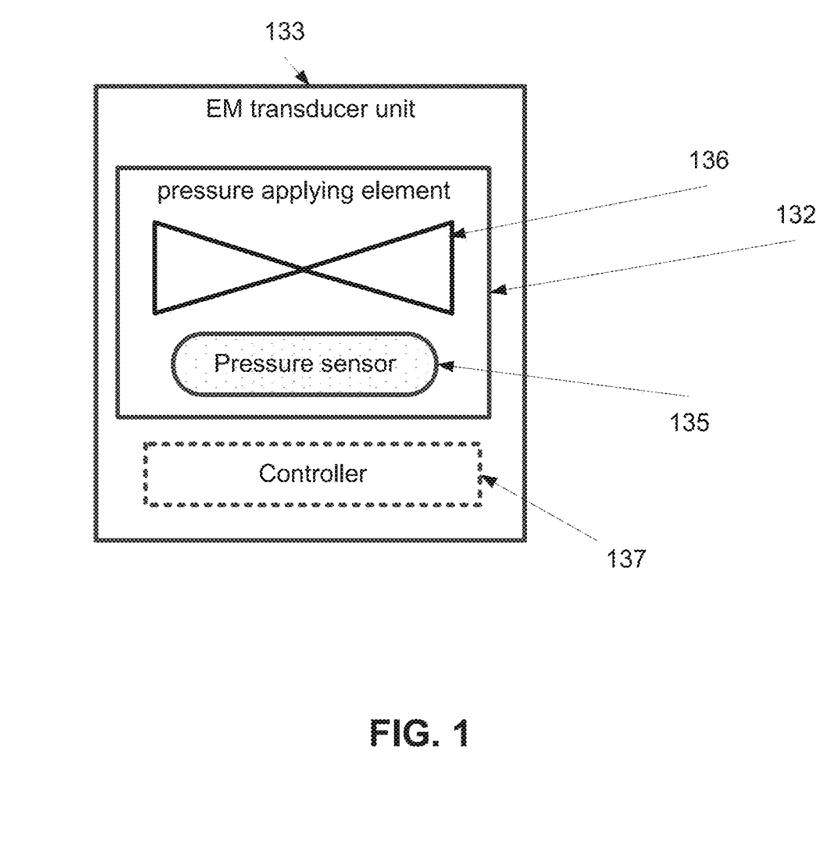
FIG. 1 is a schematic illustration of an EM transducer unit, according to some embodiments of the present invention.

Reference is now made to FIG. 1, which is a schematic illustration of a thoracic an EM transducer unit 133 having one or more EM transducer(s) (an exemplary EM transducer 136 is depicted), a pressure applying element 132 for applying pressure on the exemplary EM transducer 136, and a controller 137, for example one or more circuitries, which control EM signal emission by the EM transducer(s) 136 (may be external) and/or the processing EM signal received by the EM transducer(s) 136 and/or the pressure applying element 132 and/or a pressure sensor 135, according to some embodiments of the present invention. The EM transducer unit 133 is optionally as defined in International Patent Application No. IL2012/050545 filed on Dec. 20, 2012, which the specification thereof is incorporated herein by reference.

The EM transducer unit 133 may be installed in an EM transducer placement portion, for example a pocket, a compartment, an opening and/or an attachment of a garment. The EM transducer unit 133 may be associated with any attachment unit that positions the EM transducer unit 133 opposite to a monitored intrabody tissue. The EM transducer unit 133 is an EM transmission and/or reception unit which includes one or more EM transducer(s) 136, comprising for example antennas with or without a housing and/or associated electronics, which are connected to the controller 137.

Optionally, the EM transducer unit 133 includes a plurality of EM transducer(s) 136, for example antennas, where each transducer 136 includes a separate pressure applicator and a separate gauge, and a plurality of the EM transducer(s) 136 are connected to a central controller. Optionally, one or more separate pressure applicators are used to apply pressure on a larger number of transducers 136, for example each pressure applicator may apply pressure on a set of 2, 4, 8 or more antennas. Optionally, pressure applicator(s) may apply pressure on only some of the transducer(s) 136. Optionally, a single gauge may be used to measure the pressure applied on a plurality of antennas. Optionally, a plurality of gauges is used to obtain the data, regardless of the number of transducers 136.

The EM transducer unit 133 is optionally designed to use RF and/or MW radiation for monitoring and/or diagnosing (including evaluating and assessing) body tissues, effects of internal physiological activities, and/or effects of external physiological activities and handling of movement effects. The EM transducer unit 133 may be a monitoring device as described in International Patent Applications published as WO2009/031149, and WO2009/031150 filed on Sep. 4, 2008, International Patent Application published as WO2010/100649 filed Mar. 4, 2010, and International Patent Application published as WO2011/141915 filed May 12, 2011, and International Patent Application No. PCT/IL2011/050003 filed Nov. 3, 2011 and US patent applications published as US 2010-0056907 (filed Aug. 20, 2009) and US 2011-0025295 (filed Jul. 30, 2010) all of which are incorporated herein by reference in their entirety.

For example, the controller 137 instructs the one or more EM transducer(s) 136 to transmit and/or receive EM signal to and/or from the human subject's thorax thereby obtains EM measurements of the lungs or a portion thereof. The EM measurements may then be analyzed, locally and/or remotely, to extract a biological parameter relating to the thorax or any part thereof, including for example a biological parameter indicative of one or more of fluid content (e.g. lung fluid) and/or motion (e.g. cardiac and/or lung motion).

The EM transducer unit 133 may be placed in a housing having a front surface shaped to be in contact with or conform to a curved portion of a human body in a standing, reclined, sitting and/or lying position, for example sitting on chair, lying in a bed, sitting on couch and/or standing.

The controller 137 may be part of the EM transducer unit 133 or external thereto. In some embodiments, a single controller may be associated with a plurality of EM transducers. In some embodiments, the functions of controller 137 may be performed by a plurality of controllers. The controller 137 is connected to the pressure sensor 135 that measures the pressure applied by the pressure applying element 132 on the EM transducer(s) 136 when the EM transducer unit 133 is placed to monitor a human subject. The pressure applied on the EM transducer(s) 136 affects the pressure applied by the EM transducer unit 133 on a respective thoracic skin surface area. Optionally, pressure is applied on the EM transducer(s) 136 indirectly and/or the pressure that is applied on the subject's skin near the EM transducer(s) 136 is measured indirectly. For example, one or more EM transducer(s) 136 may be incorporated in a garment. The garment may include one or more pressure applicators, for example in the form of an inflatable portion of the garment. By controlling the degree of inflation of the inflatable portion of the garment and gauging pressure therein, the pressure that is applied by one or more of the EM transducer(s) being remote from the inflatable portion, may be controlled and gauged. Optionally, the controller 137 of the EM transducer unit 133 instructs the pressure applying element 132. The controller 137 may control a degree of pressure that is applied on the EM transducer 136, optionally at a level of pressure that does not cause undue discomfort to the human subject. The controller 137 may be part of the EM transducer unit 133 or external thereto, and it may control the pressure of one or more EM transducer units.

Optionally, the pressure applied on the skin area of a human subject compresses soft body tissues that cover the more rigid skeleton and/or muscular systems in the anterior and/or posterior thoracic skin surface areas. The pressure may increase the mechanical coupling between the orientation of the transducer surface and the respective skeletal geometry, optionally as well as the distance between the EM transducer and a sensed intrabody region of the human subject in the dimension perpendicular to the EM transducer's surface. Optionally this also increases geometric stability, for example by reducing a degree of dislocation of the EM transducer in case of movement by the subject.

Optionally, the pressure applying element includes the subject's body or a portion thereof when she is instructed to apply pressure on the EM transducer (e/g/ by lying atop it). Optionally, the pressure applying element includes the EM transducer's weight, as it is placed atop a sensed body part. The pressure applying element 132 is optionally a linear actuator which creates linear motion that pushes the EM transducer 136 toward the body of the human subject, away from an anchoring surface of the transducer unit 133. The linear actuator may be electromechanical, mechanical, hydraulic and/or pneumatic and may be manually and/or automatically operated. For example, the pressure applying element 132 includes one or more inflatable members. Examples and further details for such structures are provided in International Patent Application No. IL2012/050545 filed on Dec. 20, 2012, which the specification thereof is incorporated herein by reference. In use, the pressure applying element 132 displaces the EM transducer 136 so as to press it tightly against the human subject's body. The degree of pressing may be controlled manually and/or automatically (e.g. by a mechanical pressure regulator set to automatically cut off and/or allow the flow of a fluid at a certain pressures) to a preset degree and/or based on feedback readings from a pressure sensor.

The pressure applying element 132 may reduce the distance between the surface of the EM transducer(s) 136 and a thoracic skin surface area, for example the skin surface in proximity to a monitored intrabody area (or increase the portion of the surface the EM transducer(s) 136 that is, directly or indirectly, in contact with the skin surface), and/or between the EM transducer(s) 136 and an intrabody area of interest under the skin by applying pressure on the EM transducer(s) 136, against pliable body tissue. This may increase the portion of EM signal, which is transmitted from the EM transducer(s) 136 and propagates into the intrabody area in a region of interest rather than travelling through unintended paths, for example on the skin.

The pressure applying element 132 may increase the repeatability of the positioning of the EM transducer(s) between different sessions where the EM transducer(s) is applied to the same subject. The pressure applying element 132 may assure that the EM transducer(s) 136 are in tight contact with the human subject's skin surface, directly or indirectly (e.g. through clothing).

Optionally, the pressure applying element 132 includes a tilting mechanism which allow the EM transducer(s) 136 to tilt in response to the human subject's body structure and composition and to repeatedly reach approximately the same position at a plurality of measurement sessions once pressure is applied, for example as described below.

Figure 2A:
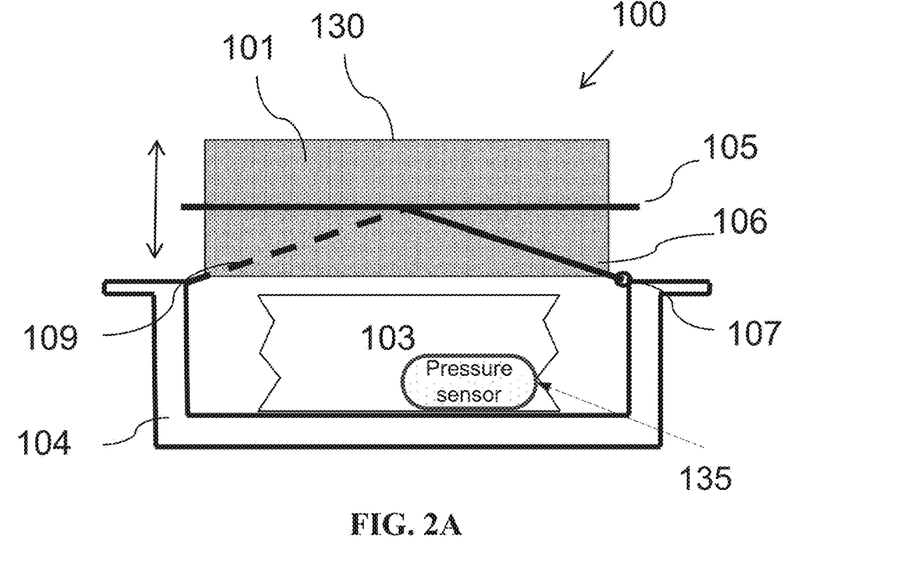
FIGS. 2A-2B are lateral and top schematic illustrations of an exemplary EM transducer unit, according to some embodiments of the present invention.
Figure 2B:
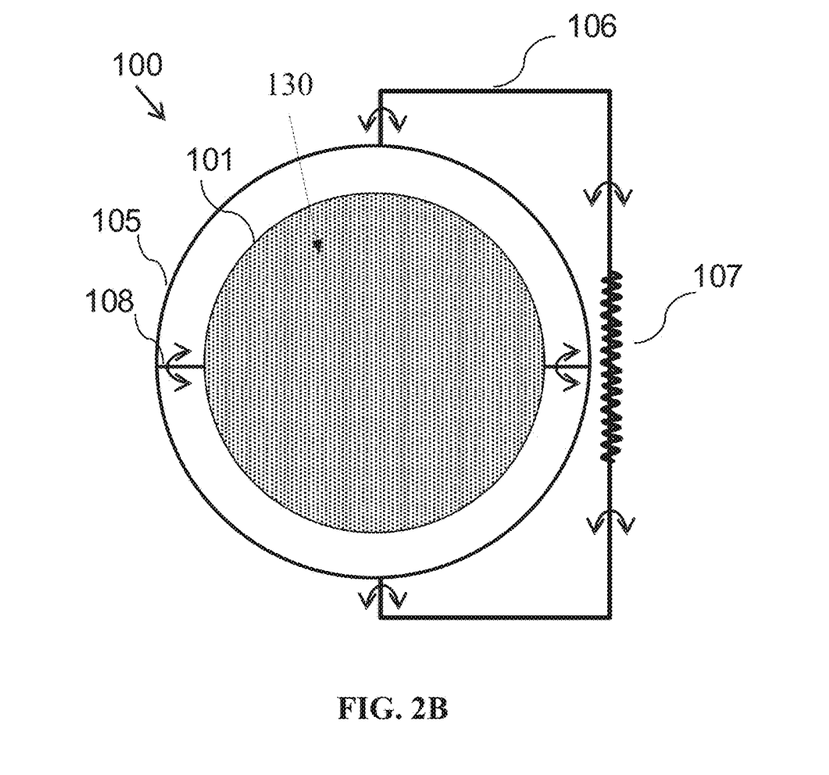

For example, reference is now also made to FIGS. 2A-2B, which are lateral and top schematic illustrations of an exemplary EM transducer unit 100, according to some embodiments of the present invention. FIG. 2A depicts a lateral view of an exemplary EM transducer unit 100 having an EM transducer 101 with a frontal surface 130 positioned slightly above an opening of a pressure applying element which includes a cup shaped housing 104 that functions as an anchoring mechanism. The cup shaped housing 104 is shown in an exemplary cross section, but may be shaped for example as a box, a cube, a dome, a cone and/or a pyramid. The housing 104 may comprise any material which is durable and/or non-elastic enough and/or rigid enough to provide support to EM transducer(s) 101 and to allow pressure to be applied to the EM transducer(s) during operation such that the frontal surface 130 is displaced and move away from the bottom of the housing toward the thoracic skin surface area.

Optionally, the housing 104 is made of or at least partially coated with an EM manipulating material, for example an EM conductive or absorbing material. The pressure applying element further includes an extendable member 103 positioned in the housing 104 to push the EM transducer 101. Extendable member 103 may be for example a pneumatic linear actuator or an inflatable member that may be inflated by a fluid, be it liquid or gas. Extendible member 103 may include for example, under and/or around the EM transducer, a spring and/or a piston operated by a motor.

In use, the EM transducer unit 100 is positioned with the frontal surface 130 facing a skin surface area of a human subject. Optionally, the EM transducer unit 100 is secured to the body of the human subject by one or more straps.

FIG. 2B depicts a top view of the EM transducer unit 100, showing an exemplary tilt mechanism having a gimbal arrangement (105, 106, also shown from lateral view in FIG. 2A) attached to an EM transducer 101. The gimbal arrangement ring 105 is connected to the EM transducer 101 by axel 108, allowing the EM transducer 101 to tilt around the axel. The gimbal arrangement ring 105 is attached to frame 106 such that the EM transducer 101 may rotate around the axis formed by the frame 106 where contacting the EM transducer 101.

As seen in FIG. 2A, frame 106 is hingedly connected to housing 104 such that the edge of the frame that is not attached to the housing may move upwards and allow EM transducer(s) 101 to move away from housing 104 as extendible element 103 extends. Optionally, arm 109 is hingedly connected to housing 104 through a first edge of the arm on one side and a second edge is slidably connected to frame 106. When EM transducer 101 is pushed away from housing 104, the second edge of arm 109 moves upwards, slides along an arm of frame 106 to move EM transducer 101 essentially vertically away from housing 104.

In some embodiments, the EM transducer 101 may be displaced vertically a distance of 2-6 cm or 3-5 cm. When extendible element 103 retracts, for example when it is deflated, EM transducer 101 is free to return into housing 104, for example by a counter pressure from the body of the human subject. This may be facilitated by exerting force in essentially the same direction, for example by spring 107. Pressure applied by the mechanical arm may be inferred from the state of the arm.

Figure 3:
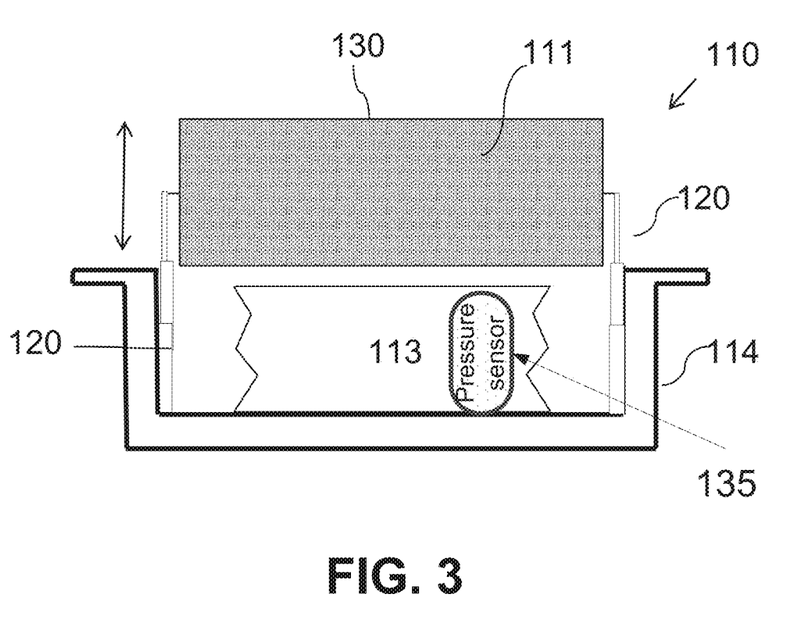
FIG. 3 is a lateral view of an alternative EM transducer unit, according to some embodiments of the present invention.

FIG. 3 depicts a lateral view of an alternative EM transducer unit 110 where an EM transducer 111 is held in housing 114 and pushed away from the bottom of the housing by an extendible element 113. In this example, the EM transducer 111 is anchored to the bottom of the housing 114 using a number of telescopic elements 120. When the EM transducer 111 is pushed away from the housing 114, telescopic elements 120 extend, holding it in position during movement. Once extendible element 113 retracts telescopic elements 120 retract and allow the EM transducer 111 to move toward the bottom of the housing 114 or even pull it in this direction.

Figure 4A:
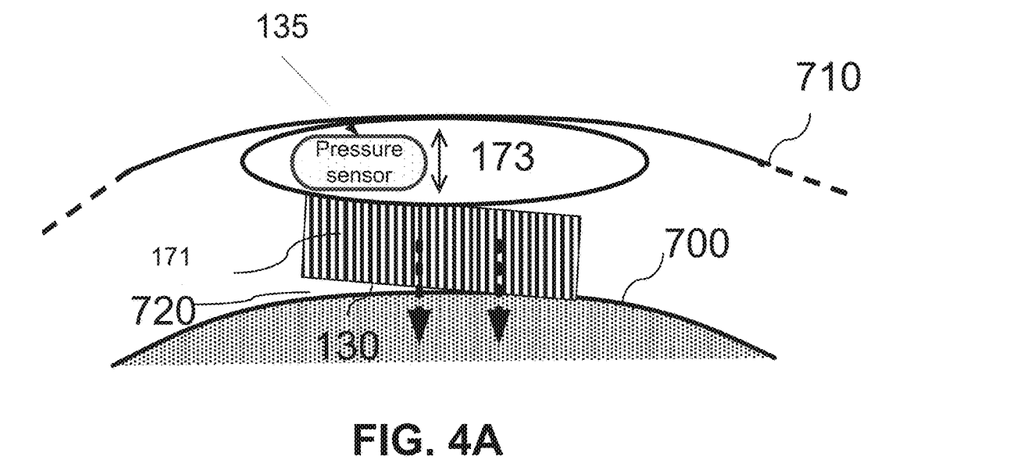
FIGS. 4A-4C are schematic cross sections of an EM transducer unit having an inflatable pressure applying element, according to some embodiments of the present invention.
Figure 4B:
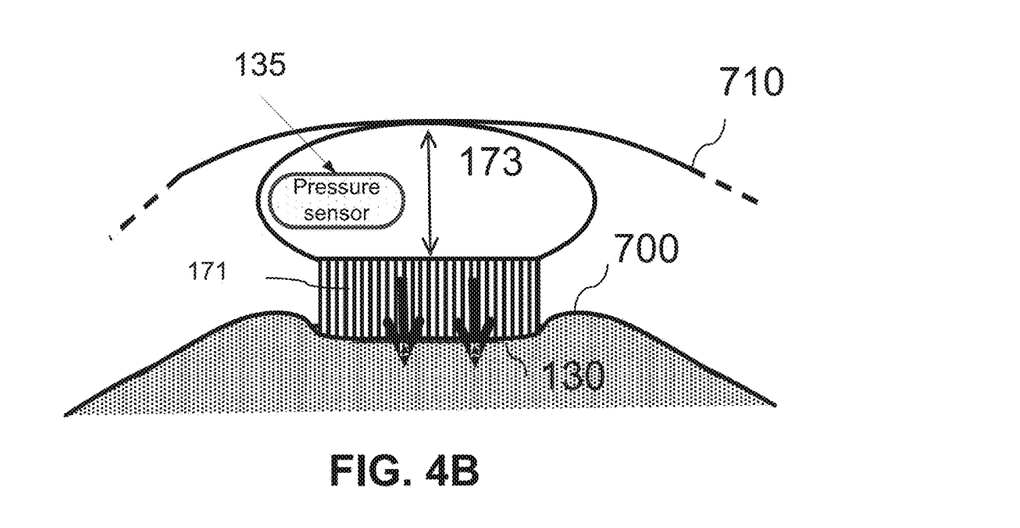
Figure 4C:
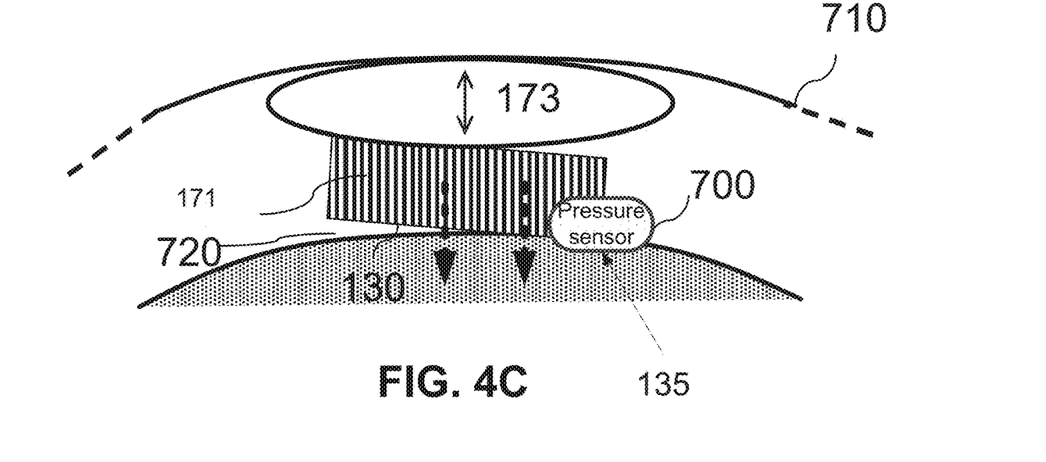

Reference is now made to FIGS. 4A and 4B which are schematic cross sections of an EM transducer unit 171, placed between a thoracic garment piece or any other surface of a wearable item 710 and a human subject body surface 700, directly or indirectly (for example above a piece of an undershirt or any other garment or fabric that is worn on the upper body or is a part of the garment), according to some embodiments of the present invention. In FIGS. 4A and 4B, the extendible member 173 is an inflatable member positioned between upper surface 710 and EM transducer 171 that is respectively depicted in partly deflated and inflated states. As used herein inflating and deflating are performed by streaming fluid (liquid and/or gas). While the upper surface is fitted to some degree of tightness to the human subject and hence exerts a low pressure on body surface, for example a in the direction depicted by dashed arrows, it is loose enough to allow the EM transducer surface 130 to tilt with respect to body surface 700. The tilt forms a gap 720 between EM transducer surface 130 and the body surface 700. As extendible member 173 and the EM transducer 171 are sandwiched between a relatively non-elastic upper surface, for example a garment portion, 710 and the human subject's body, extension of extendible member 103 caused EM transducer 171 to apply a higher degree of pressure on the human subject's body surface 700, depicted by bold line arrows in FIG. 4B. Since the human subject's body comprises pliable tissue(s) at the area shown, the body part compresses slightly under the pressure and surface 130 of EM transducer 171 is brought to full surface contact with body surface 700. Such an arrangement as shown in FIGS. 4A and 4B (including an EM traducer unit 171 and extendible member 173) may in some embodiments be sewn into a garment, with a layer of material (e.g. a fabric or cloth) placed under EM transducer 171 (not shown). Thus, when in use, the layer of material will come between EM transducer surface 130 and the body surface 700. Optionally, as depicted in FIG. 4C, the pressure sensor is external to the pressure applying element, for example measures a pressure applied on a body surface, for example measures a tension applied on a strip.

Optionally, the above mentioned pressure controller (not shown) controls the degree of displacement of the EM transducer 101, 111 or 171 from within its housing or from its support (e.g. upper surface 710) and towards the body and/or the pressure exerted by the EM transducer(s) mechanism on the human subject and/or the pressure exerted on the EM transducer(s). The EM transducer surface 130 may be pushed from a resting position in a housing and towards a human subject's body by 0.5 or more centimeters (cm). For example, this may be between 0 cm and 7 cm or more, for example between 3 cm and 5 cm or more.

Optionally, the pressure level applied on the EM transducer 101, 111 or 171 may be between 100 millibar (mbar) and 600 mbar, for example between 200 mbar and 400 mbar or about 300 mbar within inflatable member 173 or and/or between 0.01 Kg/cm$^2$ and 0.3 Kg/cm$^2$ on the human subject's body. The degree of pressure may be set to be the same for a plurality of measurements to ensure repeatability of the pressure and/or comparability of measurements taken at different times. This may be controlled for example by a gauge, a pressure sensor, to provide feedback control for a pneumatic or hydraulic pump which pumps fluid into the inflatable member 173 or 113 or 103 and/or by use of a displacement sensor. Optionally, pressure may be controlled manually. Optionally, the outcome of the gauge, a pressure and/or a displacement degree, is displayed to allow a manual pressure adjustment. Alternatively or additionally, it may be desired to take EM measurements at a plurality of different pressure/displacement settings.

Additional mechanisms may be used for retracting an EM transducer form a position where it applies pressure on a human subject's body. For example, in some embodiments, an EM transducer may be retracted by releasing pressure from an inflatable member 103, 113 or 173 and allowing for gravity and/or a retracting motion of the extendible member or a portion thereof to pull the EM transducer.

Additionally or alternatively one or more springs and/or elastic components that are attached, directly or indirectly to the EM transducer and an anchoring position can be used (for example spring 107 as described above). When an extendible member extends and displaces the EM transducer, the spring and/or elastic components extend as well. Once the extendible member retracts or reduces the pressure applied on the EM transducer, the spring and/ elastic components snap back to position, pulling the EM transducer with them.

In order to reduce the chance of the EM element displacing once an inflatable member is deflated (e.g. during undressing and/or redressing), a mechanism may be used to manually or automatically lock the EM transducer in place. This function may be provided at least partly, the aforementioned spring and/or elastic components. Additionally or alternatively, to reduce unintentional inflation of an inflatable member (even if partial) a valve in the inflatable member that might allow fluid into the inflatable member is shut, thereby preventing fluid from flowing back into the inflatable member (e.g. air from the environment).

Figure 5A:
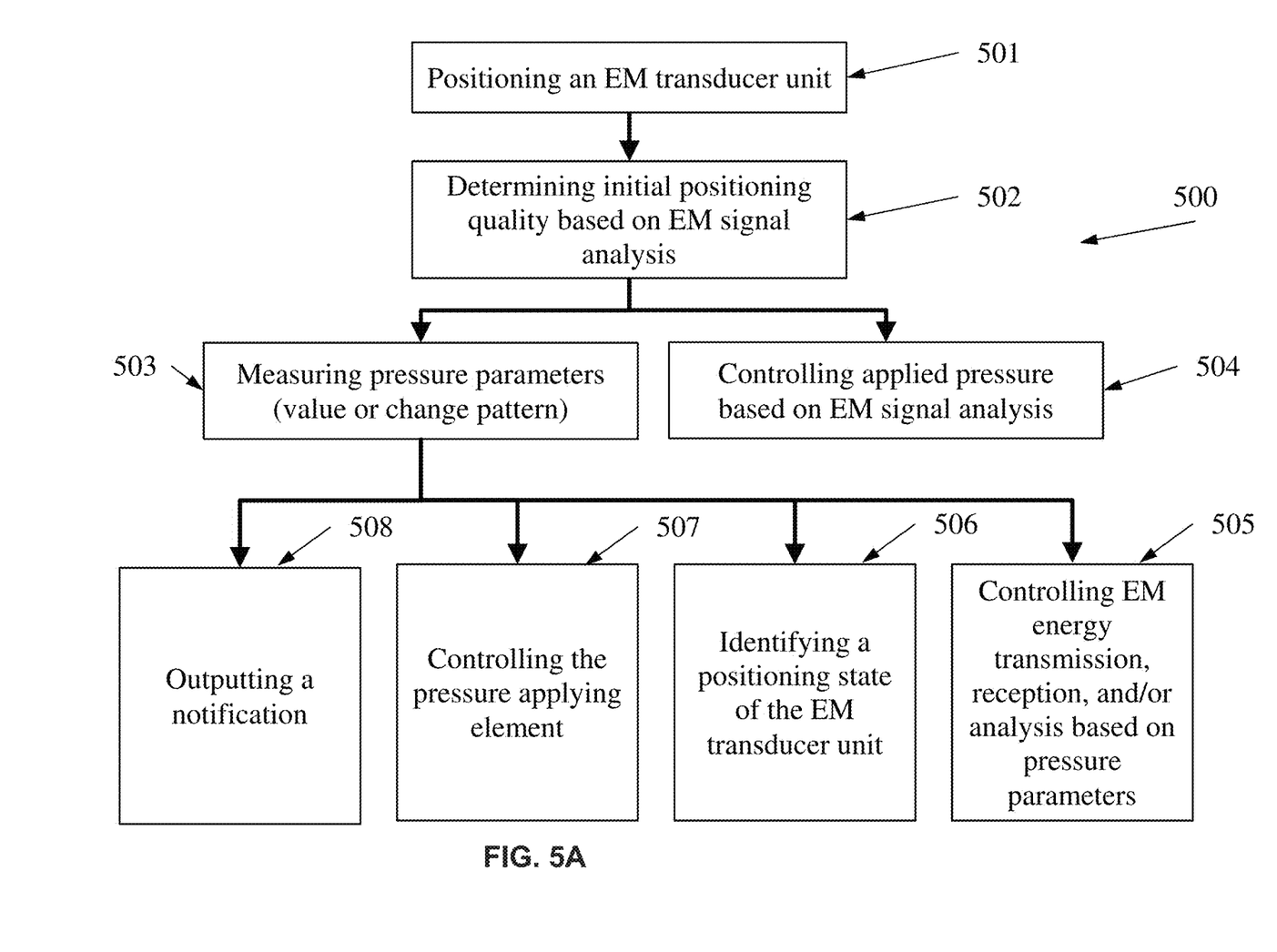
FIG. 5A is a flowchart of a method of controlling transmission and/or reception of EM signal and/or the analysis of such EM signal based on parameters related to pressure applied on a skin area, according to some embodiments of the present invention.

Reference is now also made to FIG. 5A, which is a flowchart of a method 500 of controlling transmission and/or reception of EM signal and/or the analysis of such EM signal based on parameters related to the pressure applied when pressing an EM transducer unit, such as 133, on a skin area, according to some embodiments of the present invention. The EM signal may be transmitted from EM transducer(s), such as 136, through a thorax of a user (reflections from a single direction and/or through the thorax from side to side). The method may be implemented for example by any of the above described EM transducer units.

As shown at 501, the method is performed when an EM transducer unit having one or more EM transducer(s) and a pressure applying element, for example such as EM transducer unit 133 depicted in FIG. 1, is positioned to transmit and/or intercept RF and/or MW radiation for monitoring and/or diagnosing body tissues, for example the thoracic tissues, for instance the lungs. As described above, a garment may be worn to position the EM transducer unit 133. Alternatively, the EM transducer unit 133 is detachably coupled to the body of a human subject using strap(s) and/or stickers and/or a dedicated garment in such a manner that pressure applied on the EM transducer(s) by the pressure applying element presses the EM transducer(s) against the human subject's skin, directly or indirectly (e.g. through light clothing or a layer of fabric).

Optionally, as shown at 502, the EM signal received by the one or more EM transducer(s), for example 136, is analyzed to determine the quality of the initial positioning of the EM transducer unit. The quality may be defined in a binary manner, namely proper or improper positioning or valued along a scale, for example a positioning quality. For example, received EM signal, for example a reflection or a signal passing through the body of the human subject, for example through the thorax, is considered valid if it is attenuated by a level higher than a threshold, for example of 30 dB. The received EM signal may be signal that is transmitted by the same EM transducer or one or more EM transducers being adjacent the transmitting one and/or EM signal transmitted by one or more other EM transducers being for example at an opposing side of the subject.

Attenuation below the threshold may indicate that the EM transducer unit is not tightly attached to the human subject body or that it is not properly positioned, for example when the EM transducer(s) are tilted with respect to the body surface or the pressure applying element was activated before being applied to the subject. Additionally or alternatively, the received EM signal is analyzed to detect a signal variation indicative of breathing, for example a match to a pattern. Additionally or alternatively, the received EM signal is analyzed to detect characteristics of a signal for example frequency response, phase response. The detection of a match with a pattern, such as a breathing pattern, or expected signal characteristic, may be used as an indication that the signal properly interacts with a thorax of a breathing human subject's. Optionally, the EM signal is the same signal that is used by the EM transducer unit for monitoring or diagnosing the human subject. For example, the signal that is used for measurement of breathing is used to ensure proper positioning during measurement, for example as described herein. This may be performed once during measurement and/or intermittently and/or constantly during measurement. Optionally, the power of the EM signal that is used to ensure proper positioning of the EM transducer, for example before measurement and/or during a break in measurement, is 5% or less, for example 1% or less, than the power used for monitoring or diagnosing the human subject. Transmitting designated EM signal (s) may be performed before and/or during the measurement.

Optionally, the pressure applying element 132 is activated after a proper positioning is confirmed. Optionally, proper positioning is confirmed after at least some pressure is applied.

As shown at 503, one or more pressure parameters, for example value(s) or pressure change pattern(s), are measured during and/or after the positioning of the EM transducer unit 133, for example by pressure sensor 135(s). The pressure parameters may include a pressure applied at the touching point between the EM transducer 133, for example, the frontal surface of the one or more EM transducer(s) 136 and the skin surface of the human subject and/or a pressure measured in or on the mechanism of the pressure applying element 132, for example in an inflatable member of the pressure applying element 132 and/or on a mechanical arm of the pressure applying element 132.

Optionally, the pressure change pattern is indicative that pressure exceeds and/or falls below a given threshold abruptly before and/or during measurement. Based on the analysis of the pressure parameters, transmission may be prevented, imitated and/or terminated.

Optionally, as shown at 504, the pressure applied by the pressure applying element 132 is controlled, for example reduced and/or increased, based on an analysis of the EM signal captured by the EM transducer(s) 136 and optionally current pressure parameter(s) measured by the pressure sensor 135(s). For example, when an incompatibility is identified between the current pressure parameter(s) and an analysis of the EM signal, for example in a pattern of a signal, instructions for the pressure applying element 132 are calculated. The incompatibility may be a mismatch between the current pressure parameter(s) and an expected EM signal reception pattern. These instructions allow controlling the applied pressure based on the identified incompatibility, for example a pressure increment or decrement. For example, once EM signal indicative of a proper positioning of the EM transducer unit 133 is identified, the pressure applying element 132 increases pressure applied on the EM transducer(s).

Additionally or alternatively, as shown at 505, in use, the pressure parameters are analyzed, for example by the controller 137 and optionally based also on an analysis of the EM energy captured by the EM transducer(s) 136, to control EM signal transmission and/or reception, for example based on detection of a proper positioning of the EM transducer unit(s) 133. Optionally, the controller is set to initiate an operation session wherein EM signal is transmitted for monitoring and/or diagnosis only when the pressure parameters confirm proper positioning. One example for adjusting transmission and/or reception is in detail in FIG. 5B, and another detailed example of controlling analysis of EM signal or adjusting transmission and/or reception based on movement estimation, for example breathing movement estimation, is provided below with reference to FIG. 6.

In one example, the EM transducer unit 133 is integrated in a garment. When the subject wears the garment, the pressure applying element 132 may start applying pressure, for example inflating an inflatable member. A pressure variation pattern is measured by the gauge to identify a pattern indicative of breathing movement. When this pattern is found, for example for at least 4 respiration cycles, one or more EM signal transmission session(s) are initiated. Alternatively or additionally, a pressure variation pattern is measured to detect a degree of pressure that is reached within a given period, this may be indicative of a wearing by a subject when pressure is applied. Additionally or alternatively, the pressure variation pattern may be used to identify proper positioning. When this pattern is found, one or more EM signal transmission session(s) are initiated. The captured EM signal may now be correlated according to the movement pattern. Optionally, when pressure drops and/or breathing movements cannot be identified, the EM transmission session(s) are halted.

Additionally or alternatively, as shown at 506, the pressure parameters are analyzed, for example by the controller 137, to identify a positioning state of the EM transducer unit 133, for example to confirm proper positioning and/or to detect disengagement and/or to provide positioning information to a human subject and/or a caregiver while the EM transducer unit 133 is attached to the body of the human subject. For example, an increase in the pressure correlated with a mechanical action of the pressure applying element 132 to press the EM transducer(s) 136 against the body of the human subject is indicative that the EM transducer unit is properly located. For example, the increase in the pressure is expected to reach a given threshold within a given timeframe when the EM transducer unit is properly located.

Additionally or alternatively, as shown at 507, once the measured pressure parameters are in a predetermined pressure range and/or a predefined pressure change pattern has been identified, pressure may be maintained within a given range by controlling the pressure applying element. For example, pressure on the body surface may be maintained within a 150 gr/cm$^2$ window or within a 75 gr/cm$^2$ window or within a 45 gr/cm$^2$ window or even within a 15 gr/cm$^2$ window (e.g. about 240 gr/cm$^2$, 245 gr/cm$^2$ or 250 gr/cm$^2$).

Optionally, the pressure change is of less than 10%, less than 5%, less than 1% and/or less than any other intermediate percentage.

Optionally, the controller 137 is set to instruct the pressure applying element 132 to maintain a pressure within a fixed range to reduce the effect of the a posture change during and/or between measurements. The controller 137 instructs the pressure applying element 132 to increase or reduce the applied pressure, for example to inflate or deflate an inflatable member, to maintain pressure within a certain range during the measurement(s). The pressure may be increased and/or decreased so as to maintain an essentially fixed degree during measurement, despite fluctuations that might result, for example, by the user's breathing and/or slight movements or a leak from the pneumatic system.

Additionally or alternatively, as shown at 508, if a deviation between the measured pressure and an expected pressure pattern or value exceeds a given threshold one or more of the following indications may be outputted:

an indication that the EM transducer unit is positioned differently than in prior measurements;

an indication that the EM transducer unit is not positioned properly;

an indication that the system cannot or should not perform a monitoring or diagnosis of body tissue(s) due to a movement, a posture, an emotional agitation, and/or that the measured breathing pattern is not of a healthy subject, for example in case of an irrelevant sickness that might affect the intended measurement; and Different indications may be issued based on the timing of the detection of the deviation and/or a match with a respective pressure change pattern reference and/or a set of threshold ranges each associated with another notification.

Optionally, the notification is forwarded to a caregiver, for example via a proxy, such as an email server, a mobile communication device, and/or another network connected device that forwards the notification as an email, a cellular message, an transmission control protocol internet protocol (TCP-IP) message and/or the like. Optionally, the notification is presented to the user, for example on a man machine interface (MMI) associated with the human subject. Optionally, measurements gathered when a deviation is identified are disregarded and/or analyzed in a special manner (e.g. as long as agitation is sensed and until the pattern returns to be within the threshold). Alternatively, the deviation is taken into account in the analysis of the measurements, affecting the monitoring and/or diagnosis.

Figure 5B:
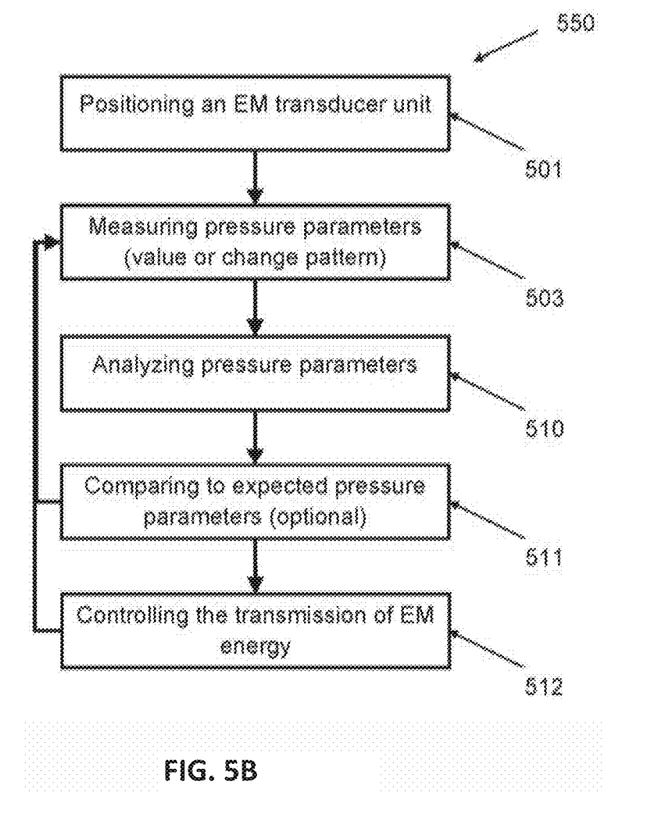
FIG. 5B is a flowchart of a method of controlling transmission and/or reception of EM signal based on parameters related to the pressure applied on a skin area, according to some embodiments of the present invention.

Reference is now also made to FIG. 5B, which is a flowchart of a process 550 of controlling EM signal, such as 132, based on a analysis of pressure parameters, according to some embodiments of the present invention. Blocks 501 and 503 are as described with reference to FIG. 5A; however blocks 510, 511 and 512 are as described below identified.

As described above, the EM transducer unit 133 may be placed to monitor a tissue (e.g. thoracic tissue). As pressure is applied, pressure buildup is measured. As shown in 510, the pressure parameters are analyzed, for example by the controller 137, to identify a positioning state of the EM transducer unit 133, for example to confirm proper positioning (e.g. to ensure sufficient mechanical coupling with between the orientation of the transducer surface and the respective skeletal geometry) and/or to detect disengagement and/or to provide positioning information to a human subject and/or a caregiver while the EM transducer unit 133 is attached to the body of the human subject. Optionally this is performed as shown in 511 by comparing the measured parameters to an expected value, or set of values or patterns.

The expected parameters may be predetermined for example, based on some average relating to the general population or a part thereof or may include data that was obtained based on one or more previous measurements of the same subject.

In 512, the transmission of EM signal is controlled based on the pressure measurements and their analysis. For example, an increase in the pressure correlated with a mechanical action of the pressure applying element 132 to press the EM transducer(s) 136 against the body of the human subject is indicative that the EM transducer unit is properly located. For example, the increase in the pressure is expected to reach a given threshold within a given timeframe when the EM transducer unit is properly located. Additionally or alternatively, the threshold may be adjusted based on a prior measurement of the same patient. Optionally the pressure increase pattern in one or more measurement sessions is stored and at a later measurement session a new pattern is compared with stored data to confirm a sufficient degree of a match. In case of a mismatch, measurement may be prevented, a notification may be given, and/or instruction may be provided to adjust the positioning of the EM transducer(s) 136.

Figure 6:
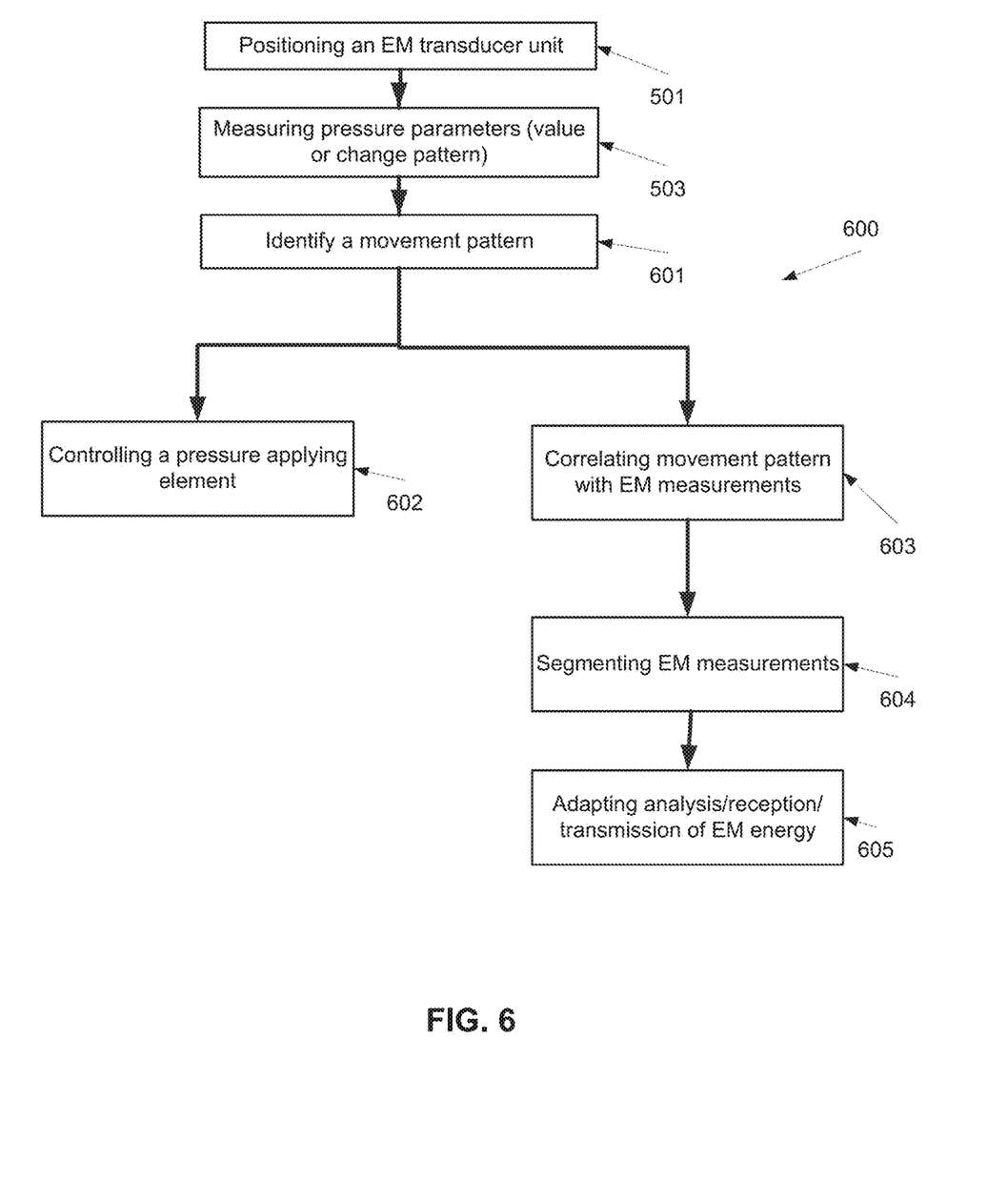
FIG. 6 is a flowchart of a process of controlling EM signal and/or pressure applying elements based on a movement pattern that is inferred from an analysis of pressure parameters, according to some embodiments of the present invention.

Reference is now also made to FIG. 6, which is a flowchart of a process of controlling EM signal and/or pressure applying elements, such as 132, based on a movement pattern, for example a breathing pattern or a cardiac system related pressure variation, that is inferred from an analysis of pressure parameters, according to some embodiments of the present invention. Blocks 501 and 503 are as described with reference to FIG. 5A; however blocks 601 and 602 are as described below identified.

As described above, the EM transducer unit 133 may be placed to monitor thoracic or other tissues. In such embodiments, additionally or alternatively, as shown at 601, the pressure parameters which are received and analyzed, for example by the controller 137 as described above, to identify a movement pattern of the monitored human subject and/or an organ thereof.

Optionally, movement pattern estimation is calculated, for example breathing pattern estimation and/or cardiac system activity estimation. Breathing pattern estimation may include estimation of breathing related parameters such as depth of breath, rate of breath, frequency of inhale and exhale, frequency of variation in any one or more parameters of breathing. The estimation may be based on breathing statistic and/or a breathing function. Cardiac system activity estimation may include estimation of heart rate and/or ejection fraction and/or blood flow related parameters.

Optionally, the breathing pattern estimation and/or cardiac system activity estimation is compared with a breathing pattern associated with a sub population to which the user belongs (e.g. based on age, gender, race, etc.). Optionally, a user's breathing pattern and/or cardiac system activity (or pressure variation) is recorded in one or more monitoring sessions and a new pressure variation is compared to a saved value or group of values to indicate a degree of match between a measured breathing pattern and a saved pattern.

Optionally, as shown at 602, the pressure applying element 132 may be operated based on the identified movement pattern and/or pressure value, for example to increase and decrease pressure synchronically with a movement of the human subject and/or an organ thereof, for example synchronically with the breathing movement of the thorax. As such synchronic movement reduces pressure changes which are an outcome of the breathing movement; artifact(s) caused by the breathing movement are also reduced.

Optionally, the pressure applying element 132 of one EM transducer unit 133 may operated based on the identified movement pattern and/or pressure value, for example to increase and decrease pressure synchronically with another pressure applying element 132 of another EM transducer unit 133, where pressure parameters are analyzed from one or both pressure applying elements 132.

In such embodiments, pressure may be controlled to maintain a distance between two EM transducer units 133, for example when one EM transducer unit 133 is on the back of the human subject and other is on the chest, essentially fixed.

Optionally, as shown at 603, the identified movement of the monitored human subject, for example the identification of the breathing pattern or cardiac system activity, is correlated with EM measurements which are captured from monitored and/or diagnosed body tissues. Optionally, as shown at 604, the EM measurements are segmented based on the identified movement, for example by registration or correlation of the identified movement with the EM measurements. Optionally, as shown at 605, the analysis of the corresponding EM measurements is controlled based on the measured pressure parameters. Additionally or alternatively, the reception of the EM measurements may be controlled based on the measured pressure parameters. Additionally or alternatively, the transmission of EM signal which corresponds with the EM measurements may be controlled based on the measured pressure parameters.

Optionally source separation is performed between two or more physiological processes that may affect EM signal measurement, for example heart movement artifacts and breathing movement patterns. Accordingly, analysis of the EM measurements may include identification of a pressure pattern indicative of a movement pattern, correlating the sensed EM signal with the pattern in order to remove from the EM measurement variation that is attributable to the detected pattern. For example, by detecting and eliminating the effect of a breathing pattern one may increase signal to noise ratio (SNR) relating to heart movement, and by detecting and eliminating the effect of heart movement (or heartbeat) one may increase SNR relating to lung function.

For example, a pressure variation pattern may be used to direct the analysis of corresponding EM measurements according to a breathing cycle movement pattern which is detected based on the analysis of the pressure parameters therein. This may include, for example, the sampling of EM measurements at reference points and calculating dielectric parameters based on these samples, by adding, subtracting, averaging, filtering or other such analyses. For example, the timing of maximum exhale and/or maximum inhale may be detected based on an analysis of pressure parameters. Optionally, correlation or registration of the EM measurement signal to the pressure variation pattern may be performed as part of the analysis. This may be used to facilitate extracting the dielectric parameters of body tissues, such as the lungs, in an improved manner by reducing various measurement artifacts for example artifacts related to EM noise originating from an external source and/or by EM signal that travels through undesired pathways. Another example is estimating breathing volumes from an analysis of a pressure pattern, where longer breath cycles are correlated with larger pressure changes during a respiratory period, and using these breathing volumes to direct the analysis of corresponding EM measurements.

Optionally, as exemplified below, specific points of a breathing cycle (e.g. maximum inflate and maximum deflate) may be identified from pressure change analysis and used for analyzing EM measurements. Alternatively, EM measurements may be analyzed to extract the breathing cycle.

Figure 7:
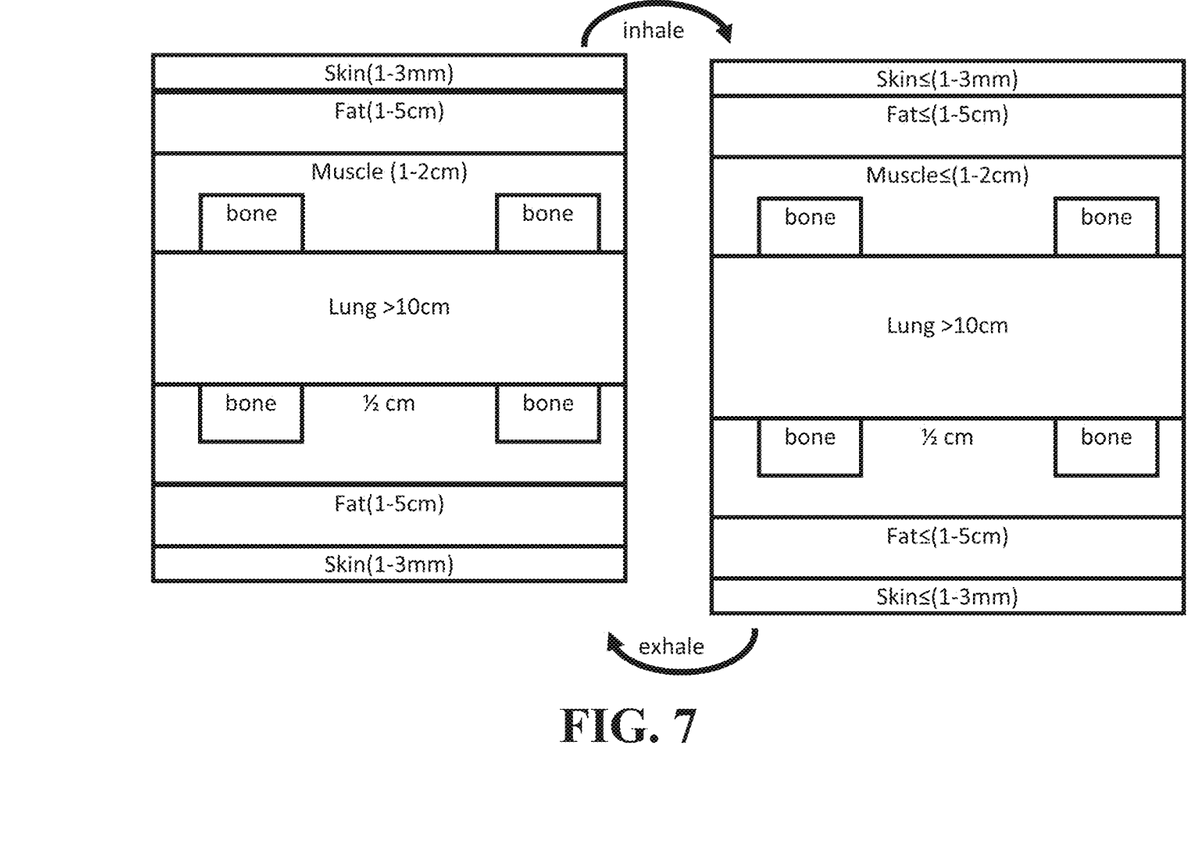
FIG. 7 is a schematic illustration depicting the differences between a geometric thoracic model in a maximum exhale state and a maximum inhale state, as calculated according to some embodiments of the present invention.

Additionally or alternatively, the pressure variation pattern which is an outcome of the movement of the monitored human subject and/or organs thereof, for example the lungs, is used for inferring anatomical parameters, for instance related dimensions of the thorax. For example, anatomical parameters, such as respiration rate, may be estimated based on the period between the time of the end of exhalation and the time of the end of inhalation. The anatomical parameters may be used to correlate/calibrate or select a geometric thoracic model used during the measurement analysis. For example, some or all of the layers of a geometric thoracic model may be continuously updated to reflect breathing movement. For example, FIG. 7 is a schematic illustration depicting the differences between a geometric thoracic model in a maximum exhalation state and a maximum inhalation state, as calculated according to some embodiments of the present invention. For instance, lung dimension increases in inhalation. Each of the muscle, skin and/or fat dimensions may be slightly narrower or assumed to be unchanged, etc. The updating may be inferred from historical pressure measurements and/or updated in real time. Optionally, the variation in pressure is correlated to infer a volume of air inhaled, exhaled and/or present within the lungs at the time of measurement. Optionally, calibration includes measurements of pressure during inhaling/exhaling of a known or measured amount of gas (or air). This may be correlated to geometric dimensions (e.g. taken using a caliper), measured pressure and/or EM measurements.

It is expected that during the life of a patent maturing from this application many relevant systems and methods will be developed and the scope of the term a gauge, a module, a controller, and a processor is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of analyzing electromagnetic (EM) signal of a human subject, comprising:
    positioning an EM transducer unit in front of a skin area opposite a target intrabody volume of a human subject, said EM transducer unit having at least one EM transducer and at least one pressure sensor;
    measuring at least one pressure parameter indicative of a pressure applied on said skin area using said at least one pressure sensor, wherein said at least one pressure parameter comprises a pressure change pattern;
    measuring EM signal using said at least one EM transducer; and
    performing an analysis of said EM signal to infer at least one intrabody parameter of said target intrabody volume;
    wherein at least one of said analysis, a transmission of said EM signal, and a reception of said EM signal is controlled according to said at least one pressure parameter.

2. The method of claim 1, wherein said pressure is a variable pressure applied by a pressure applying unit of said EM transducer unit.

3. The method of claim 2, wherein said pressure applying unit comprises an inflatable mechanism; wherein said at least one pressure parameter is measured in an inflatable member of said inflatable mechanism.

4. The method of claim 2, wherein said pressure applying unit comprises a mechanical element; wherein said at least one pressure parameter is set according to a state of said mechanical element.

5. The method of claim 2, wherein said at least one pressure parameter indicative of a movement of an organ of said human subject; further comprising controlling said pressure applying unit to increase and decrease said pressure synchronically with said movement.

6. The method of claim 1, wherein said target intrabody volume is a thoracic intrabody volume of lungs of said human subject.

7. The method of claim 1, further comprising deriving, based on said analysis, a thoracic fluid volume value.

8. The method of claim 1, further comprising detecting when said EM transducer unit is properly positioned in front of said skin area by a pressure parameter analysis of said at least one pressure parameter, and transmitting said EM signal when said EM transducer unit is properly positioned in front of said skin area.

9. The method of claim 1, further comprising detecting when said EM transducer unit is not properly positioned in front of said skin area by a pressure parameter analysis of said at least one pressure parameter and outputting a notification indicative that said EM transducer unit is not properly positioned in front of said skin area.

10. The method of claim 1, further comprising detecting a period during which that said EM transducer unit is improperly positioned in front of said skin area based on a pressure parameter analysis of said at least one pressure parameter and preventing a transmission by said EM transducer unit during said period.

11. The method of claim 1, wherein pressure change pattern is indicative of a breathing process.

12. The method of claim 11, wherein said controlling is used to reduce breathing induced artifacts in EM measurements.

13. The method of claim 1, wherein pressure change pattern is indicative of a cardiac system related process.

14. The method of claim 13, wherein said controlling is used to reduce cardiac system induced artifacts in EM measurements.

15. The method of claim 1, wherein said controlling is used to separate lung related EM variations from cardiac EM variations.

16. The method of claim 1, wherein said at least one pressure parameter comprises a tension of a strip supporting said EM transducer unit at a given location.

17. The method of claim 1, further comprising controlling said pressure applying unit to maintain said pressure within a predefined range on said skin area.

18. The method of claim 1, further comprising comparing the pressure change pattern to a threshold.

19. The method of claim 1, wherein the pressure change pattern comprises an expected signal characteristic.

20. The method of claim 1, further comprising comparing a measured value to the pressure change pattern.

\* \* \* \* \*